US008770542B2

(12) United States Patent
Loth et al.

(10) Patent No.: US 8,770,542 B2
(45) Date of Patent: Jul. 8, 2014

(54) VALVE FOR CONTROLLING A FLOW OF A FLUID THROUGH A FLUID CHANNEL, SYSTEM AND MULTIPLE-WAY VALVE

(75) Inventors: Andreas Loth, Berlin (DE); Florian Bühs, Berlin (DE); Kristian Plückhahn, Berlin (DE)

(73) Assignees: Mt. Derm GmbH, Berlin (DE); Technische Universität Berlin, Berlin (DE)

( * ) Notice: Subject to any disclaimer, the term of this patent is extended or adjusted under 35 U.S.C. 154(b) by 366 days.

(21) Appl. No.: 12/973,433

(22) Filed: Dec. 20, 2010

(65) Prior Publication Data

US 2011/0297854 A1 Dec. 8, 2011

(30) Foreign Application Priority Data

Jun. 2, 2010 (EP) .................................... 10164760

(51) Int. Cl.
*F16K 7/04* (2006.01)

(52) U.S. Cl.
USPC .................................................. 251/7; 251/4

(58) Field of Classification Search
USPC .................................................... 251/4, 7, 5
See application file for complete search history.

(56) References Cited

U.S. PATENT DOCUMENTS 3,544,060 A 12/1970 Herbert et al.
4,262,876 A * 4/1981 Willatt ............................. 251/7
4,285,492 A * 8/1981 Bujan ............................... 251/7
4,403,764 A 9/1983 Repplinger
5,257,770 A * 11/1993 Grove ............................... 251/4
5,402,823 A 4/1995 Cole
5,429,615 A * 7/1995 Starchevich ...................... 251/7
5,568,912 A 10/1996 Minami et al.
5,593,392 A * 1/1997 Starchevich ...................... 251/4
5,704,584 A 1/1998 Winterer et al.
6,280,148 B1 8/2001 Zengerle et al.

(Continued)

FOREIGN PATENT DOCUMENTS

DE 19706513 C2 8/1998
DE 29919199 U1 2/2000

(Continued)

OTHER PUBLICATIONS

European Search Report, directed to EP10164760, mailed on Nov. 18, 2010, 6 pages.

*Primary Examiner* — John Bastianelli
*Assistant Examiner* — Andrew J Rost
(74) *Attorney, Agent, or Firm* — Smith Patent Office

(57) ABSTRACT

The invention relates to a valve for controlling a flow of a fluid through a fluid channel, comprising a tube of flexible material in which a section of a fluid channel is formed, a valve component assigned to the tube, a squeeze element, which is formed and configured on the valve component by pressing against an outside surface of the tube to control a flow of a fluid through the fluid channel, optionally up to the closing of the fluid channel, a guide section, which is formed on the valve component, and a guide assigned to the valve component, which cooperates with the guide section in a relative movement of the guide and valve components relative to one another in the longitudinal direction of the tube, such that the squeeze element is displaced in the relative movement, changing the pressure on the outside surface of the tube and thus changing the flow through the fluid channel.

14 Claims, 3 Drawing Sheets

Figure 1:
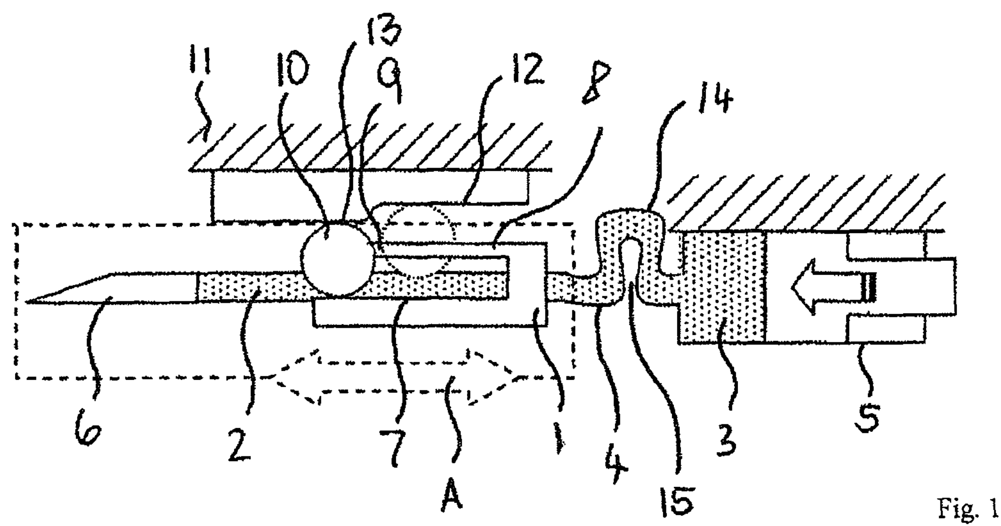

11 10 13 9 12 8 14
6 2 7 A 1 4 15 3 5

(56) References Cited

U.S. PATENT DOCUMENTS

| | | | | |
|---|---|---|---|---|
| 6,345,553 | B1 | 2/2002 | Adler et al. | |
| 6,505,530 | B2 | 1/2003 | Adler et al. | |
| 2002/0069726 | A1 | 6/2002 | Adler et al. | |
| 2005/0010236 | A1 | 1/2005 | Frister | |
| 2005/0072806 | A1* | 4/2005 | Spray et al. | 251/4 |
| 2006/0020283 | A1 | 1/2006 | Lisec | |
| 2006/0147313 | A1 | 7/2006 | Zengerle et al. | |
| 2006/0171854 | A1 | 8/2006 | Koltay et al. | |
| 2007/0083223 | A1 | 4/2007 | Kluge | |
| 2007/0181835 | A1 | 8/2007 | Hanada | |
| 2008/0033356 | A1 | 2/2008 | Kluge et al. | |
| 2008/0033470 | A1 | 2/2008 | Kluge et al. | |
| 2010/0030152 | A1 | 2/2010 | Lee et al. | |
| 2010/0036317 | A1 | 2/2010 | Oginski et al. | |

FOREIGN PATENT DOCUMENTS

| | | | |
|---|---|---|---|
| DE | 69325591 | T2 | 2/2000 |
| DE | 10337484 | A1 | 3/2005 |
| DE | 102007036265 | A1 | 2/2009 |
| EP | 1495782 | A1 | 1/2005 |
| EP | 1618915 | A1 | 1/2006 |
| EP | 1698812 | A1 | 9/2006 |
| EP | 1699560 | B1 | 9/2006 |
| EP | 1743673 | A1 | 1/2007 |
| EP | 1882491 | A1 | 1/2008 |
| EP | 1882492 | A1 | 1/2008 |
| EP | 2149388 | A1 | 2/2010 |
| WO | 9316308 | A1 | 8/1993 |
| WO | 9608666 | A1 | 3/1996 |
| WO | 2005020828 | A1 | 3/2005 |

* cited by examiner

VALVE FOR CONTROLLING A FLOW OF A FLUID THROUGH A FLUID CHANNEL, SYSTEM AND MULTIPLE-WAY VALVE

The invention relates to a valve for controlling a flow of a fluid through a fluid channel, a system having at least one valve and a multiple-way valve.

BACKGROUND OF THE INVENTION

Such valves are used to adjust and modify the volume flow of a fluid through a fluid channel. It is known in this context that the flow of the fluid through the channel is to be controlled by exerting pressure from the outside on a tube in which the fluid channel is formed, such that the pressure is adjusted as a function of a desired volume flow of the fluid through the channel.

In medical technology, dosing of volume flows takes place, for example, through microvalves or directly through a corresponding pump with which the fluid to be dispensed is acted upon with pressure. Valves are used in medicine and in the cosmetic field, for example, in injection of medically and cosmetically active substances. In addition to the injection of substances for fat reduction or for injection beneath wrinkles, dosed dispensing of a substance is also necessary for application of ink for tattooing or permanent makeup in the cosmetic field. In addition to various vaccinations, medical applications also include, for example, mesotherapy. In these applications, in addition to the simple application of the media, simultaneous administration of multiple media is also provided, so that the media react with one another only after being applied.

The dosing of the fluid may be performed by means of a contact method or a noncontact method. The fluid-dispensing device thus either does or does not come in contact with the skin. Noncontact devices are also referred to as so-called dispensers. The process of delivering the fluid is itself known as dispensing, jetting or pulsing. This dosing serves to apply substances to the skin or in subsequent substance delivery systems (cf. EP 1 882 491, for example). Contacting may be understood as dosing onto or through a surface.

All these applications have in common the need for accurate dosing. Problems are often presented by chemical or fluid properties or particles or variable media.

The document DE 103 37 484 B4 describes a noncontact dosing system, in which a tube is squeezed at a high speed, so that a free-flying droplet of liquid is formed. Dosing frequencies of 50 Hz may be achieved in this way. The design here is an open system without a prepressure. The liquid fills the tube because of the capillary forces, but the maximum dosing quantity and dosing frequency are limited by this design. If there is a backpressure, functioning is very limited or impossible.

The document DE 693 25 591 T2 describes valve system for switching a flow through flexible tubes. Two positions (bistable open/closed) are selected via a pivotable lever. The liquids should flow through the valve at the coupled flange of this construction, which is manufactured by casting and welding. Possible contamination of the liquid is not prevented, nor can this principle be used as a disposable part or for higher frequencies (>1 Hz).

The document EP 1 699 560 B1 describes one possibility for pipetting extremely small quantities, but is based essentially on a combination of traditional pipetting systems and the known PipeJet method, i.e., a tube deformation, embodied in this case as a pipette tip. It is thus possible here to dose only extremely small particles which fly through the air to their destination. This method cannot be used for injections because it is impossible to work at a backpressure.

The document DE 197 06 513 C2 describes a micro-dosing method based on a pressure chamber having a reservoir connection and a fluid outlet. The pressure chamber is reduced in size by a displacement mechanism, so that the fluid is forced to the outlet. A device for detecting the position of the displacement mechanism is essential here.

The document US 2010/0030152 A1 describes a therapeutic micro-needle system, in which multiple cannulas are used instead of one cannula.

SUMMARY OF THE INVENTION

The object of the invention is to provide improved technologies in combination with valves for controlling a flow of a fluid through a fluid channel, with which reliable control of the volume flow of the fluid is ensured, in particular even in high-frequency operation of the valve.

This object is achieved according to the invention by a valve for controlling a flow of a fluid through a fluid channel set forth herein. In addition, a system of at least one valve and a multiple-way valve is also provided and described herein. Advantageous embodiments of the invention are described herein.

The invention comprises the idea of a valve for controlling a flow of a fluid through a fluid channel, comprising a tube of a flexible material, in which a section of a fluid channel is formed, a valve component assigned to the tube, a squeeze element which is formed and configured on the valve component, to control a flow of a fluid through the fluid channel by pressing against an outside surface of the tube, optionally up to the closing of the fluid channel, a guide section which is formed on the valve component and a guide assigned to the valve component, said guide cooperating with the guide section in a relative movement of the guide and the valve component relative to one another in the longitudinal direction of the tube, such that the squeeze element applies pressure to the outside surface of the tube in this relative movement, and thus displaces the flow through the fluid.

According to another aspect of the invention, a system having at least one valve and a pressure-applying device, which is in fluid connection to the fluid channel, are provided, said pressure-applying device being configured so that a pressure can be applied to the fluid in the fluid channel.

Another aspect of the invention relates to a multiple-way valve having a plurality of valves for controlling the flow of a fluid through a fluid channel.

With the inventive valve, there is the possibility of individually adjusting and regulating the volume flow through the fluid channel formed in the tube in accordance with the respective use requirements, including in particular a volume flow adjustment with high change frequencies. In one possible application, the displacement of the squeeze element produced by the relative movement of the guide and valve component and resulting change in flow through the tube can also be implemented as repeating movements, also at a high frequency. The guide assigned to the valve component can be designed to conform to the respective use case, thus providing an adequate displacement path for the squeeze element. For example, the squeeze element may be displaced from a first position, in which the fluid channel in the tube is completely open, into a second position, in which the fluid channel is essentially closed. In one type of use with this embodiment, the valve is used as a so-called closer. A reverse displacement of the squeeze element may also be provided, which then corresponds to an embodiment as a so-called opener.

The displacement of the squeeze element in the relative movement of the guide and valve component preferably takes place essentially across the longitudinal direction of the tube, but a movement of the squeeze element on a circular arc segment may also be provided, for example.

The valve may be used in any devices or device parts to control the flow of a fluid through the fluid channel in a tube. Use in a dosing unit is advantageous in particular, a medical or cosmetic active ingredient being delivered in a dosed manner with this dosing unit in the field of medicine or cosmetics. The dosing device may be embodied in a contact or noncontact design. The dosing device may, for example, be integrated into an injection device to control the dosed delivery of an active ingredient under a backpressure. In this embodiment, the valve is preferably downstream from a cannula that delivers the active ingredient. The cannula punctures the skin and can dispense the active ingredient at a predefined puncture depth, for example. The dosing device can thus be used in a method for dosed delivery of a fluid, in particular for injection into the human or animal body.

The relative movement between the guide and the valve component during use of the valve in any dosing device, which is implemented as an injection device, for example, in which the fluid may also be dispensed against a backpressure, is preferably accomplished by means of manual operation or with the help of a drive. For example, devices for puncturing human or animal skin have drive mechanisms, which move a puncture device repetitively back and forth at a high frequency. This repetitive movement may then be used for the relative movement of the guide and the valve component to open and close the fluid channel in the tube. Such puncture devices are described in DE 299 19 199 U1, EP 1 495 782 and EP 1 618 915, for example. In addition, the following documents can be cited as examples: EP 1 743 673, EP 2 149 388 and EP 1 882 492. Other technologies may also be used as the drive mechanisms: pneumatics, lifting magnetic drive, drives having rotating motors and translation into a linear movement and a piezoelectric drive. The present invention may also be utilized in its various embodiments, in particular in conjunction with such puncture or injection devices.

According to a preferred further embodiment of the invention, the valve component is formed with a reversibly displaceable cantilevered arm on which the squeeze element is arranged. The cantilevered arm may be designed in one or more parts. For example, in one embodiment, multiple cantilevered arms, optionally cooperating with one another, may be provided. The reverse displacement is preferably accomplished here on the basis of a spring elastic design of the cantilevered arm. For example, the cantilevered arm is reversibly displaced by means of a pivoting movement of the cantilevered arm. In one embodiment, the squeeze element is formed on a distal end in relation to the base of the cantilevered arm, i.e., an area in which the cantilevered arm is mounted. The squeeze element is preferably formed on the cantilevered arm with a protrusion in the direction of the tube, which presses against the tube from the outside. A squeeze surface of the squeeze element assigned to the tube may have any surface contour, for example, a rounded surface, a spherical surface, or a surface with a squeeze edge, which is formed in the area of two surfaces running obliquely to one another. A combination of such surface contours may also be provided, in particular for optimizing the squeeze effect.

In an expedient embodiment of the invention, it is possible to provide for the cantilevered arm to extend along the tube and to optionally form an acute angle with the longitudinal direction of the tube. In one embodiment, the cantilevered arm runs essentially parallel to the longitudinal direction of the tube.

According to an advantageous embodiment of the invention, the guide section is formed on the squeeze element. In this embodiment, the squeeze element additionally assumes the functionality of cooperation of the valve component and the guide assigned to the valve component. The squeeze element is then embodied as an integrated element, namely as a combined squeeze and guide element on which the guide section is formed. For example, in a relative movement of the valve component and the guide in one embodiment, a surface section of the squeeze element slides along the guide assigned to the guide component.

According to a further embodiment of the invention, the guide is preferably formed on a wall section. The wall section may be formed on a housing in which the valve component and tube are accommodated, for example. Then according to one embodiment, a housing part is moved with the wall section formed thereon in operation in relation to the valve component, and the guide section of the valve component here then glides along the guide on the housing part, so that the squeeze element is displaced, which leads to a change in the flow through the fluid channel. Conversely, it is possible to provide for the valve component to move inside the housing, so that again the guide section slides along the guide formed on the housing part, which leads to displacement of the squeeze element. Furthermore, both the valve component and the wall section with the guide formed on it may move. In these or other embodiments, it is possible to provide for the displacement of the squeeze element and thus the change in the flow through the fluid channel to occur repetitively at a frequency between approximately 10 Hz and approximately 500 Hz, preferably between approximately 50 Hz and approximately 150 Hz. Alternatively, use in a single-puncture mode is also conceivable, in which then only one single puncture or one injection is performed after manual triggering by the user.

In an advantageous embodiment of the invention, it is possible to provide for the valve component to be designed as a microvalve component. In this way, the valve is suitable for a micro-dosing device, for example.

A further embodiment of the invention may be provided, in which the squeeze element is designed to surround at least half of the tube.

According to a preferred further embodiment of the invention, the squeeze element is formed by a plurality of partial squeeze elements, which are arranged around the tube. In one embodiment, the squeeze elements are arranged on a shared base. It is possible to provide for the plurality of partial squeeze elements to be moved jointly, based on the relative movement of the guide and the valve component. This movement may take place similarly and/or simultaneously. In a preferred embodiment, the plurality of partial squeeze elements is formed in a rotationally symmetrical arrangement around the tube. In a further embodiment of the invention, the arrangement of the plurality of partial squeeze elements is embodied essentially according to a pressure-reducing mechanism.

In an expedient embodiment of the invention, it is possible to provide for the at least one part of the plurality of partial squeeze elements to be arranged so they are supported on one another at least in one end position. It is possible to provide here for individual partial squeeze elements to be supported on one another in the end position in which the fluid channel is partially or completely closed by squeezing of the tube, so that further closing of the fluid channel is no longer possible in one embodiment.

According to an advantageous embodiment of the invention, a fastening of the squeeze element on the valve component is formed to allow a high-frequency displacement of the squeeze element in the relative movement for opening and at least partial closing of the fluid channel in the tube. Such an embodiment may be formed with the above-mentioned cantilevered arm, for example.

A further embodiment of the invention preferably provides for the valve component to be embodied at least partially as an injection-molded part. Injection-molded parts are inexpensive and can also be manufactured by mass production. In these or other embodiments, it is possible to provide for the valve component to be embodied as a disposable product. In a further embodiment, the injection molding of the valve component may be embodied in a two-component injection molding process (2C injection molding). In one embodiment, the valve having the at least one valve component, a tube section, the guide section and optionally a cannula connected to the tube section may be designed as a disposable module. Such a disposable module may be connected to a drive mechanism in a single step.

In one advantageous embodiment of the invention, it is possible to provide for the valve component to be arranged on the tube. In one embodiment, the valve component is designed to sit on the tube, preferably detachably. For example, the valve component may be arranged on the tube by means of an elastic clamping action, which is preferably provided by the squeeze element and the counterpart assigned to the squeeze element. According to a further embodiment, the valve component in this embodiment is designed with a tube guide, along which the tube runs in at least some sections when the valve component is arranged thereon. In one embodiment, the tube guide and the cantilevered arm having the squeeze element run essentially in parallel with the longitudinal direction of the tube, for example, above and below the tube.

A further refinement of the invention may provide for the fluid channel to run through a compensating section, which at least partially compensates for the relative movement of the guide and the valve component. With the help of the compensating section, a displacement of the valve component with a tube section fixedly arranged thereon is tolerated in the relative movement with respect to a stationary tube section, for example, by means of a tube section with one or more open loops. If the compensating section is arranged downstream from a cannula, for example, then a repeated puncturing movement of the cannula can be compensated in this way. Such an embodiment may be provided in particular in a dosing device or an injection device for dosed dispensing of a fluid, for example, a medical or cosmetic active ingredient.

In conjunction with the system having at least one valve and a pressure-applying device, which is in fluid connection with the fluid channel, the integration of this system into a dosing device for dosed dispensing of a fluid may be provided, in particular a medical or cosmetic substance. The fluid dispensing may be performed here under the influence of a backpressure, which is important in conjunction with injections in particular. For example, such an injection device is used in combination with a device for tattooing or for forming permanent makeup. In this case, the dispensing of an ink is controlled by the valve, but the dosing of another cosmetic active ingredient or a medicinal substance may also be provided.

In the case of a multiple-way valve, it may be provided in one embodiment that the fluid channels arranged side by side next to one another are adjusted with regard to the flow passing through them. In one embodiment, an integrated valve component, which serves to control the volume flow in multiple fluid channels, is provided. To this end, the integrated valve component has a plurality of squeeze elements, each being assigned to a tube with the fluid channel formed therein. In a multiple-way valve, intersections between fluid channels may also be designed.

A series connection of multiple valve components may be suitable for increasing the dosing accuracy, inasmuch as the volume between the valve components, for example, contains a fluid under pressure and only the volume stored in between is dispensed by skillful opening and closing. For example, a corresponding valve may consist of tubes of different wall thicknesses or of tube-and-pipe combinations. The "storing" tube section need only be capable of storing energy which maintains an excess pressure in this section (balloon with an inlet and an outlet). This is of interest for the purely mechanical embodiment in particular. It is possible to interconnect multiple valves and this may be utilized, for example, to represent multiple-way valves (cf. FIG. 3). Other components may thus also be connected after the valve component.

The valve may also be used for intake or suction. A combination of the two may also be provided, for example, intake and discharge in alternation or in multiple stages in succession (for example, in, in, out, out, out, out, etc.). This may be used for tattoo removal, for example, during which active ingredients are injected into the tattoo and the tattoo pigments are removed by suction. This method of tattoo removal as such is described in the document WO 2005/020828, for example.

One advantage of the invention is the possibility of that predosed or variable and/or crystallizing/drying media may be dosed without damaging the system or having to clean it because the fluid transport takes place only in a system that is easy to change.

DESCRIPTION OF PREFERRED EXEMPLARY EMBODIMENTS OF THE INVENTION

Figure 2:
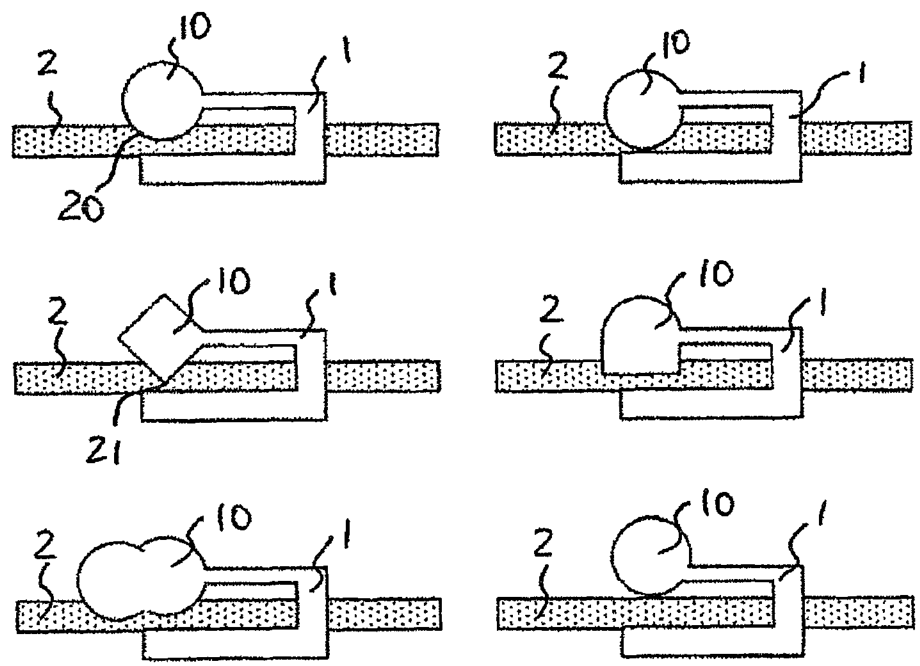
Figure 3:
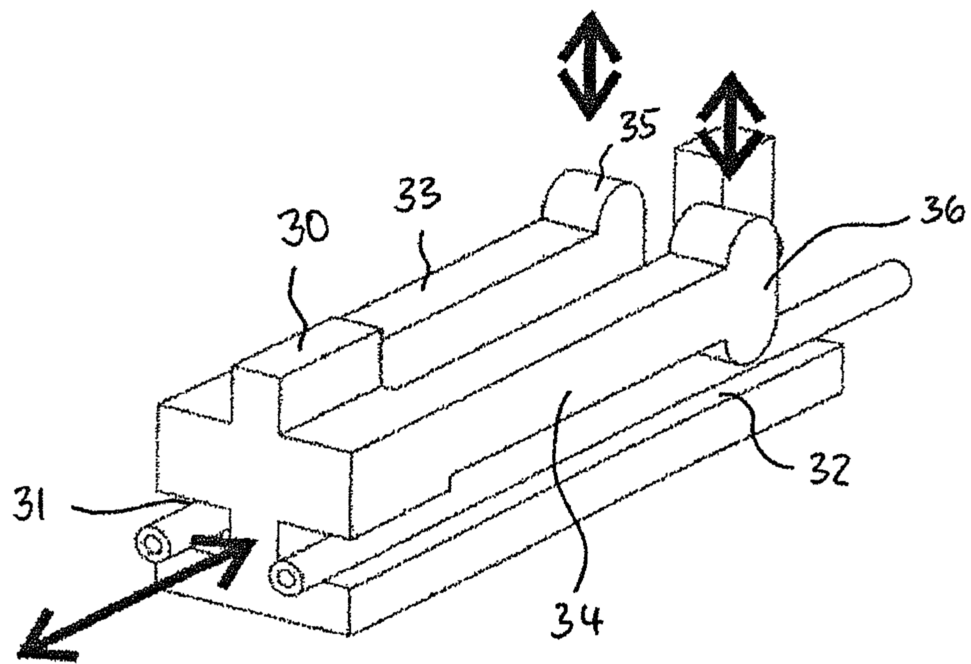
Figure 4:
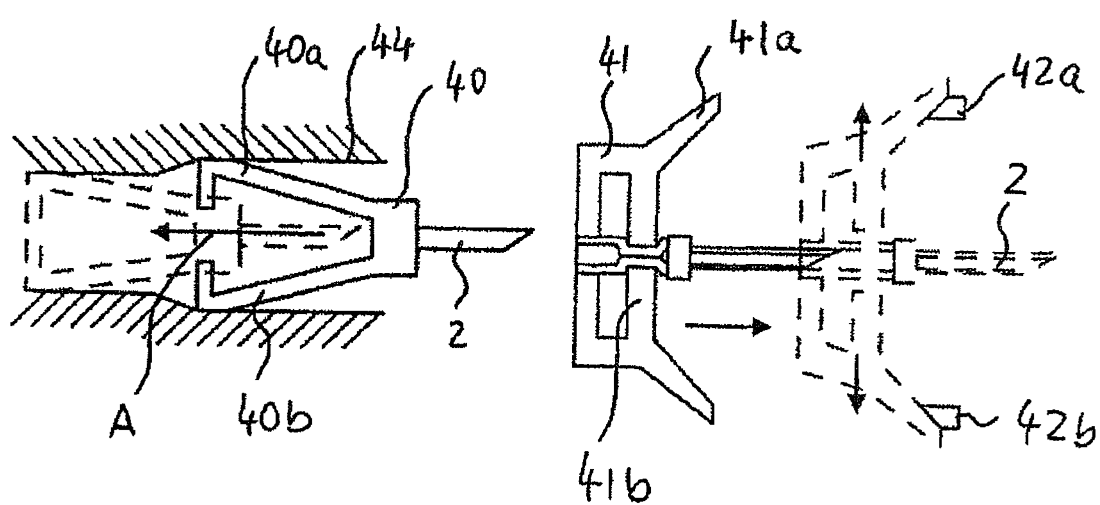
Figure 5:
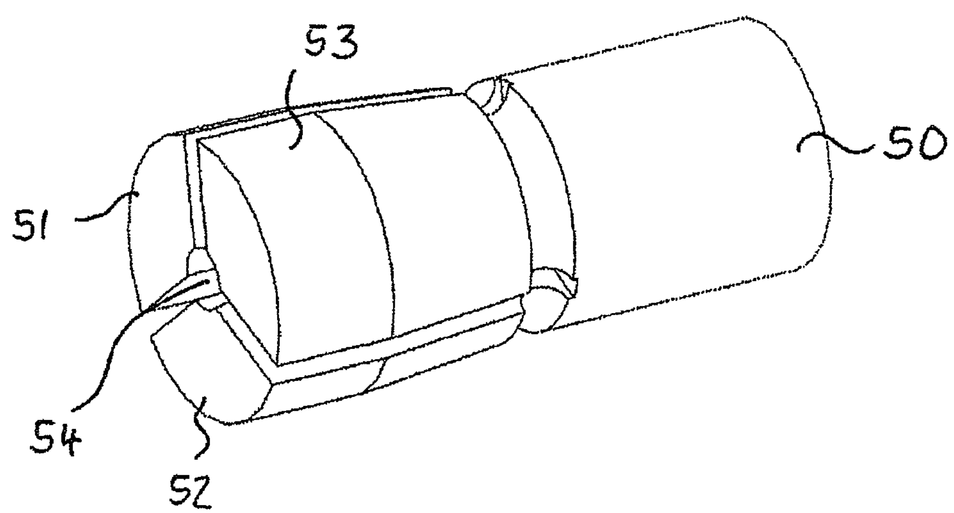

The invention is explained in greater detail below on the basis of preferred exemplary embodiments with reference to drawings in figures, in which FIG. 1 shows a schematic diagram of a system having a valve, FIG. 2 shows multiple embodiments of a valve component, FIG. 3 shows a schematic diagram of a multiple-way valve in which two fluid channels run parallel to one another, FIG. 4 shows a schematic diagram of a system having a partial valve, and FIG. 5 shows a schematic diagram of a valve component having a plurality of partial squeeze elements.

FIG. 1 shows a schematic diagram of a system having a valve component 1, which is arranged on a tube 2, in which a fluid channel 4 for a fluid 3 is formed, through which the fluid 3 from a reservoir 5 which is acted upon by pressure reaches a cannula 6, where the fluid is dispensed in dosed form. The reservoir 5 may be, for example, a reservoir for ink, which is used to form a tattoo or permanent makeup. In another embodiment, the reservoir may contain, for example, a substance for injection under wrinkles.

The valve component 1 is formed with a tube guide 7 on which the tube 2 rests. A cantilevered arm 8 is formed opposite the tube guide 7. A squeeze element 10 is arranged on the distal end 9 of the cantilevered arm 8, pressing on the tube 2 from the outside when the valve 1 is arranged in the relative position shown in FIG. 1 with respect to a wall section 11 having a guide 12 formed therein. When the valve component 1 (cf. arrow A in FIG. 1) is moved in relation to the guide 12 in the longitudinal direction of the tube 2, a guide section 13 slides on the squeeze element 10 along the guide 12. The squeeze element 10 is displaced across the longitudinal direction of the tube 2 in this way, so that the fluid channel 4 formed in the tube 2 is opened and closed. The relative movement between the valve component 1 and the guide 12 thus permits dosed dispensing of a fluid 3 through the cannula 6.

A compensating section 14 is formed in an area downstream from the fluid channel 1, compensating for the movement of the valve component 1 and the tube section thereby moved along with it relative to the reservoir 5. To this end, the tube 2 in the compensating section 14 forms an open loop 15.

By means of the respective squeeze element, the volume flow can be adjusted for a known medium by regulating the applied pressure, the opening width or the time. These parameters influence the amount of dosable substances and/or viscosities. In principle, any liquid and gaseous substances with particles that are not too large in comparison with the inside diameter of the tube can be dosed in this way.

The respective clamping or squeezing device may be operated purely mechanically by a movement of the clamping device in a guide having a corresponding wall design which causes the clamp formed by the squeeze element to be opened and closed. The clamping action can be reset via the elastic deformation and/or restoring forces of the tube and/or by the pressure of the medium in the tube on the tube wall. Dosing can be performed at a high frequency in this way.

The valve component with the squeeze element may be fixedly connected to the tube or attached to it subsequently. In the latter case, the valve may be embodied as a multiple-way valve. Because of its low manufacturing cost, for example, when made of plastic by the injection molding method, and its better handleability, disposable use is to be given preference but variants comprised of other materials, such as metal, composite materials or the like are also possible.

In its various embodiments, the valve component may operate as an opener or a closer. A continuous change in the volume flow may be achieved. The pressure may be applied to the tube from one or more sides. One-sided is understood here to mean that the volume cross section is limited from one side; for example, the squeeze element presses from one side on a tube that is fixed on a substrate with respect to the squeeze element. In the two-sided case, the valve component to the principle of tongs or forceps is conceivable according (cf. FIG. 4), where the clamping jaws are guided opposite one another.

FIG. 2 shows multiple embodiments of the valve component 1, where the squeeze element 10 is formed with different geometric designs accordingly. In particular a surface form in a squeeze section 20 of the squeeze element 10 facing the tube 2 is designed in a different manner. A rounded surface, a spherical surface, a planar surface and a surface area having a squeeze edge 21 belong here.

FIG. 3 shows a schematic diagram of a multiple-way valve in which a double-valve component 30 having parallel tube guides 31, 32 is formed. A respective squeeze element 35, 36 which presses on the respective tube from the outside is formed on the respective cantilevered arms 33, 34.

FIG. 4 shows a schematic diagram of two valve component (cf. right and left sides in FIG. 4) in which the respective squeeze element 40, 41 is formed with the respective clamping jaws 40*a*, 40*b* and 41*a*, 41*b*, which are moved toward or away from one another in a relative movement of the respective valve component 40, 41 along a guide 44. In one embodiment on the left side in FIG. 4, the clamping jaws 40*a*, 40*b* are spaced a distance apart from one another in a starting position and are prestressed against being pressed together. If the valve component 40 moves along arrow a, the clamping jaws 40*a*, 40*b* are moved toward one another, so that pressure is exerted on the tube 2 arranged between the clamping jaws 40*a*, 40*b*. The dotted lines on the left side of FIG. 4 show a state in which the clamping jaws 40*a*, 40*b* close the tube 2 having the fluid channel.

In the diagram on the right side in FIG. 4, the dotted lines represent a position of the valve component 40, in which the clamping jaws 41*a*, 41*b* are pressed apart from one another with the help of stops 42*a*, 42*b*, so that the fluid channel in the tube 2 is released.

FIG. 5 shows a schematic diagram of a valve component 50 in which multiple partial squeeze elements 51, 52, 53 are arranged around a tube guide 54. The valve component 50 is formed for a type of "pressurized ink" mechanism" in which the partial squeeze elements 51, 52, 53 are moved toward one another (closing the tube) or away from one another (opening the tube) due to the relative movement of the valve component 50 and the guide (not shown in FIG. 5).

In preliminary investigations, dispensing frequencies of up to 100 Hz have been achieved. The dosed droplets were separated completely from the end of the tube in either the horizontal position or in the vertical position. Distilled water was used as the test fluid at a pressure of 2 bar and a tube diameter of 0.7×0.3 mm (outside to inside). Clean separation of the individual droplets was verified using a high-speed camera at a recording frequency of 1,500 Hz. The test setup was made of plastic on a miniaturized scale. The dimensions of the functioning valve were 4×4×15 mm.

Application ranges are found in injection of medical and cosmetic substances in particular. Integration into a bundle of complete needles of a puncture or injection device may be provided, just as it is also possible to operate multiple cannulas simultaneously. Examples of cosmetic treatments that can be mentioned include carboxy therapy, i.e., injection of $CO_2$, for example, for fat reduction, injections beneath wrinkles at depths of 1.0 to 4.0 mm using a wide variety of media, tattooing and tattoo removal (cf. EP 04 770 455, which refers only to superficial suction removal there) at depths of 1.0-3.5 mm or application of permanent makeup at depths of 0.3-1.0 mm. Suction removal from the skin is conceivable in general for both cosmetic and medical application. Purely medical applications include not only various vaccinations at depths of 0.2-0.6 mm but also mesotherapy at depths of 0.2-10 mm.

The following list represents a selection of possible substances that may be applied: hyaluronic acid, vitamins, Q10, vaccines, therapeutic antibodies, cancer antibodies, diabetes therapeutic agents, hormones, cytokines, biochemical or biological signal substances, antioxidants, hair growth agents, hair growth inhibitors, mineral substances to improve skin tone and skin metabolism, enzymes, coenzymes, amino acids, nucleic acids, inert pigment particles, inert skin fillers, nerve-activating ingredients such as botox or bacterial toxin, diabetic control agents such as color-changing particles, which depend on the glucose level.

For all applications, in addition to the simple administration of media, this simultaneous administration of multiple media is also conceivable; these media should react with one another only after the injection, for example. Some of the applications have in common the introduction or removal of a wide variety of media at a defined depth and/or at a certain point in time. The importance of the precise depth of a vaccination can be seen clearly in the intracutaneous vaccination technique in particular. The active ingredient to be administered as a vaccine loses a substantial portion of its effect when the target depth is exceeded by more than 15%.

In addition to packaging extremely small quantities of medium, such as expensive medications, the desired mixing ratio can be adjusted extremely easily, for example, with several different tube diameters.

Especially in areas such as vaccination technique, even reagents that are very difficult to handle can be used easily because they can be used in a closed container with a valve and therefore do not come in contact with the actual dispenser. It is thus possible to avoid tedious cleaning of the devices.

It is also conceivable to use a sealing liquid, comparable to a cork, for example, a hydrophilic active ingredient and a hydrophobic sealing substance to thus prevent the substance administered from running off. A high-viscosity sealing substance may also be used for this purpose. Alternatively, the closure of the skin may be implemented by coagulation with HF, laser or other thermal effects.

The present invention in its various embodiments can be combined with other technologies, for example, with measurement of the depth of skin layers and the anatomical adjustment of the optimum layer depth of the needle. The substances may be injected accurately into the predefined skin strata. The measurement and layer depth technology is described in document EP 188 2493, for example.

Based on the simple design, the numerous operating variants and the small design height, the invention can be integrated with minimal effort into a variety of different products.

The features of the invention disclosed in the above description, the claims and the drawing may be important individually as well as in any combination for the implementation of the invention in its various embodiments.

The invention claimed is:

1. A valve for controlling a flow of a fluid through a fluid channel, comprising:

a tube of flexible material in which a section of the fluid channel is formed, a valve component assigned to the tube, a squeeze element which is formed and configured on the valve component by pressing against an outside surface of the tube to control a flow of a fluid through the fluid channel, optionally up to the closing of the fluid channel, a guide section, which is formed on the valve component and a guide assigned to the valve component, which cooperates with the guide section in a relative movement of the guide and the valve component relative to one another in the longitudinal direction of the tube, such that the squeeze element is displaced in the relative movement, changing the pressure on the outside surface of the tube and thus changing the flow through the fluid channel, and wherein the squeeze element and the valve component are structured and arranged for high frequency displacement with a frequency between 10 Hz and 500 Hz so as to move the squeeze element to open and at least partially close the fluid channel in the tube.

2. The valve according to claim 1, wherein the valve component is formed with a reversibly displaceable cantilevered arm on which the squeeze element is arranged.

3. The valve according to claim 2, wherein the cantilevered arm extends along the tube and optionally forms an acute angle with the longitudinal direction of the tube.

4. The valve according to claim 1, wherein the guide section is formed on the squeeze element.

5. The valve according to claim 1, wherein the guide is formed on a wall section.

6. The valve according to claim 1, wherein the valve component is formed as a microvalve component.

7. The valve according to claim 1, wherein the squeeze element is formed, extending around at least half of the tube.

8. The valve according to claim 1, wherein the squeeze element is formed with a plurality of partial squeeze elements, which are arranged around the tube.

9. The valve according to claim 1, wherein the at least one part of the plurality of partial squeeze elements is arranged so they are supporting one another in at least one end position.

10. The valve according to claim 1, wherein the valve component is designed at least in part as an injection-molded part.

11. The valve according to claim 1, wherein the valve component is arranged on the tube.

12. The valve according to claim 1, wherein the fluid channel runs through a compensating section, which at least partially compensates for the relative movement of the guide and the valve component.

13. A system having at least one valve for controlling a flow of a fluid through a fluid channel, comprising:

a tube of flexible material in which a section of the fluid channel is formed, a valve component assigned to the tube, a squeeze element, which is formed and configured on the valve component by pressing against an outside surface of the tube to control a flow of a fluid through the fluid channel, optionally up to the closing of the fluid channel, a guide section, which is formed on the valve component, a guide assigned to the valve component, which cooperates with the guide section in a relative movement of the guide and the valve component relative to one another in the longitudinal direction of the tube, such that the squeeze element is displaced in the relative movement, changing the pressure on the outside surface of the tube and thus changing the flow through the fluid channel, and a pressure-applying device which is in fluid connection with the fluid channel and is configured to apply a pressure to the fluid in the fluid channel, and wherein the squeeze element and the valve component are structured and arranged for high frequency displacement with a frequency between 10 Hz and 500 Hz so as to move the squeeze element to open and at least partially close the fluid channel in the tube.

14. A multiple-way valve having a plurality of valves for controlling a flow of a fluid through a fluid channel, comprising:

a tube of flexible material in which a section of a fluid channel is formed, a valve component assigned to the tube, a squeeze element, which is formed and configured on the valve component by pressing against an outside surface of the tube to control a flow of a fluid through the fluid channel, optionally up to the closing of the fluid channel, a guide section, which is formed on the valve component, a guide assigned to the valve component, which cooperates with the guide section in a relative movement of the guide and the valve component relative to one another in the longitudinal direction of the tube, such that the squeeze element is displaced in the relative movement, changing the pressure on the outside surface of the tube and thus changing the flow through the fluid channel, and wherein the squeeze element and the valve component are structured and arranged for high frequency displacement with a frequency between 10 Hz and 500 Hz so as to move the squeeze element to open and at least partially close the fluid channel in the tube.

* * * * *